United States Patent [19]

Zähner et al.

[11] 4,287,186
[45] Sep. 1, 1981

[54] ANTIBIOTICS, A PROCESS FOR THEIR PREPARATION AND THEIR USE AS PLANT PROTECTION AGENTS

[75] Inventors: Hans Zähner, Tuebingen; Hartwig Holst, Pohlheim; Gerhard Zoebelein, Leverkusen; Adelinde Keckeisen, Tuebingen, all of Fed. Rep. of Germany

[73] Assignee: Bayer Aktiengesellschaft, Leverkusen, Fed. Rep. of Germany

[21] Appl. No.: 106,223

[22] Filed: Dec. 21, 1979

[30] Foreign Application Priority Data

Jan. 9, 1979 [DE] Fed. Rep. of Germany ....... 2900591

[51] Int. Cl.³ .............................................. A61K 31/71
[52] U.S. Cl. ................................... 424/181; 536/23; 536/24; 424/180
[58] Field of Search .................. 424/181, 180; 536/23, 536/24

[56] References Cited

U.S. PATENT DOCUMENTS

| | | | |
|---|---|---|---|
| 3,700,655 | 10/1972 | Suzuki et al. | 536/23 |
| 3,703,506 | 11/1972 | Suzuki et al. | 536/23 |
| 4,046,881 | 9/1977 | Dähn et al. | 536/23 |

*Primary Examiner*—Delbert R. Phillips
*Assistant Examiner*—Blondel Hazel
*Attorney, Agent, or Firm*—Sprung, Felfe, Horn, Lynch & Kramer

[57] ABSTRACT

A method of combating arthropods, comprising applying to the arthropods, or to a habitat infested therewith an arthropodicidally effective amount of an antibiotic which (a) is colorless, very readily soluble in water and in pyridine but insoluble in other customary organic solvents, gives a positive reaction with ninhydrin, sodium metaperiodate/benzidine and potassium permanganate and gives a yellow coloration with iron (III) chloride, (b) has the UV and IR spectra substantially as shown in FIGS. 1 and 2, (c) on chemical degradation yields uracil, an amino-hexuronic acid and an amino-acid containing a pyridine ring, (d) on paper electrophoresis proves to be an amphoteric substance and has an isolectric point at about pH 6 and (e) consists of the elements carbon, hydrogen, oxygen and nitrogen, or one or more active components of the antibiotic mixture, the active agent being applied alone or in admixture with a diluent or carrier. The antibiotic is known as Nikkomycin which is apparently a mixture of components of the formula

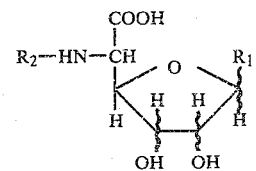

in which $R_1$ is

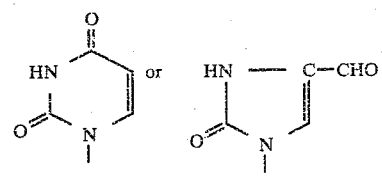

and $R_2$ is hydrogen, 4 Claims, 2 Drawing Figures

ANTIBIOTICS, A PROCESS FOR THEIR PREPARATION AND THEIR USE AS PLANT PROTECTION AGENTS

The present invention relates to the use as arthropodicides, especially as insecticides or acaricides, of certain antibiotics, some of which are known as fungicides. The invention also relates to certain of the antibiotics that are new and to a microbiological process for their preparation from strains of Streptomycetes.

It has already been disclosed that polyoxines have found broad application in plant protection as fungitoxic agents. However, the disadvantage of these compounds is their lability in alkali and, furthermore, the fact that they occur only as mixtures of variable composition and thus are difficult to meter and standardize precisely.

Furthermore, an antibiotic which is designated Nikkomycin, which as a powerful fungicidal action against phytopathogenic fungi, has been disclosed in U.S. Pat. No. 4,046,881. It has now been found that the Nikkomycin disclosed therein consists of several structurally different components and that the Nikkomycin mixture and its components or groups of components have an activity against animal pests and especially against insects and arachnids.

Accordingly, the present invention provides a method of combating arthropods, especially insects or acarids, which comprises applying to the arthropods, or to a habitat thereof, the Nikkomycin mixture or one or more of its active components, alone or in admixture with a diluent or carrier.

The invention also provides crops protected from damage by arthropods by being grown in areas in which immediately prior to and/or during the time of the growing, a Nikkomycin mixture or one or more of its active components was applied, alone or in admixture with a diluent or carrier.

The substances to be used according to the invention are produced by a submerged culture of suitable microorganisms in suitable nutrient solutions under suitable physical conditions. They are separated off from the culture solution by adsorption and precipitation and enriched by further suitable methods.

For the process of preparation, the new strain *Streptomyces tendae* Ettlinger et al Tü 901 of the order of Actinomycetales, the family of Streptomycetaceae and the genus Streptomyces can be employed. This strain has been isolated from a soil sample from Nikko, Japan. It has been filed under No. CBS 354.75 with the Centraalbureau voor Schimmelkultures, Baarn, Netherlands, under No. ATCC 31160 with the American Type Culture Collection, Rockville, Maryland, U.S.A. and under No. FRI 3136 with the Fermentation Research Institute, Osaka, Japan. This strain belongs to the genus Streptomyces and is characterized by the following properties.

(a) The spores are ellipsoidal. They are $0.4-0.6 \times 1.2-1.4\mu$ in size and have a smooth surface.

(b) The color of the air mycelium is initially chalk-white and in the ripened state is ash grey (cinereus).

(c) The spore chains are monopodially branched and arranged in loose spirals and loops.

(d) On peptone-iron agar a black pigment was formed at 27° C. The strain is chromogenic.

The characteristics taken together identify strain Tü 901 as belonging to the species *Streptomyces tendae* Ettlinger.

Nutrient media which contain the customary sources of carbon and of nitrogen and the necessary salts are used for the process for the preparation of the Nikkomycin mixture. Sources of carbon which can be used are carbohydrates, especially polysaccharides, for example starch; disaccharides, for example maltose and cane sugar; and monosaccharides, for example glucose and fructose. Furthermore, sugar alcohols, for example mannitol and glycerol, and also naturally occurring mixtures, for example malt extract, can also be used. Mixtures of any of these carbon sources may be employed. The source of nitrogen which is used can be one of the customary sources of nitrogen, for example protein substances, protein hydrolysis products, amino acids, ammonium ions, nitrate ions, naturally occurring complex substances, such as peptones, casein hydrolysis products, "corn steep liquor", soya flour and meat extract, and suitable mixtures thereof.

Auxiliary substances used in the nutrient medium are preferably the salts, for example phosphates, sulphates or chlorides, of magnesium, iron, zinc and manganese. The concentration of these substances can vary within wide limits and in some cases the necessary concentrations are contained as impurities in the above-mentioned sources of carbon or of nitrogen or in the water used.

Furthermore, anti-foams of very diverse types, for example soya oil, polyols or silicones, can also be used as auxiliaries. Buffers, including organic buffers, are used to maintain the desired pH range.

Water may be mentioned as the most important diluent for the nutrient media.

The process of preparation is generally carried out under aerobic conditions; the culture can be carried out according to conventional methods, for example using shaking cultures or aerated fermentation cultures. The percentage ratios of the constituents of the nutrient solution can vary within wide ranges. In general, the sources of carbon make up 1 to 10%, preferably 2 to 5%, by weight and the sources of nitrogen make up 0.1 to 4%, preferably 0.5 to 2%, by weight; the salts are present in the customary concentrations, preferably in the range from 0.01 to 1% by weight. The anti-foams are usually present in a concentration of 0 to 1% by weight. The temperatures used for sterilization are in general 100° to 140° C., preferably 120° to 130° C.

The pH values of the growing cultures are in general from 5.5 to 8, preferably from 7 to 7.5. The culture temperature can be between 18° and 37° C. and is preferably 27° to 30° C. It has been found that the amount of the antibiotic which becomes enriched in the culture broth in general reaches its maximum 1 to 14 and especially 3 to 5 days after the culture is started. The end point of the cultivation is determined with the aid of biological tests; in particular the action against *Botrytis cinerea* (test method according to R. Hütter et al, Arch. Mikrobiol. 51, 1–8 [1965]) and *Mucor hiemalis* (test methods according to the thesis of G. Kirst, Tübingen [1971] and also according to Kneifel et al, J. Antib. A 27, 20–27 [1974]) is determined.

When carrying out the process of preparation, a filtration can first be carried out to prepare the culture solutions, the mycelium being separated off by this means. The latter can be subjected to ion exchange chromatography on suitable ion exchangers. Chromatography can be carried out in the form of column chromatography or of preparative thin layer chromatography. The adsorbents used can be any of the customary (non-acid) inorganic or organic adsorbents, for example aluminum oxide, silica gel, magnesium silicate, active charcoal, cellulose, cellulose derivatives, synthetic resins such as polyamides, derivatives of polyamides and the like, for example acetylated polyamide, or dextran gels. Very diverse solvents or solvent mixtures in which the antibiotic according to the invention is soluble can be used as the solvent system for preparative thin layer chromatography. Subsequently, gel chromatography and isolation of the pure product in a further column with subsequent freeze-drying can be carried out.

The Nikkomycin mixture, which is the subject of U.S. Pat. No. 4,046,881 can be characterized by the following data:

(a) Solubility and properties: Nikkomycin is a colorless mixture of substances which is very readily soluble in water and pyridine and is insoluble in the other customery organic solvents, in particular aliphatic hydrocarbons, aromatic hydrocarbons, chlorinated hydrocarbons and ethers. It shows a positive reaction with ninhydrin, sodium metaperiodate/benzidine and potassium permanganate. A yellow coloration is obtained with iron(III) chloride.

Figure 1:
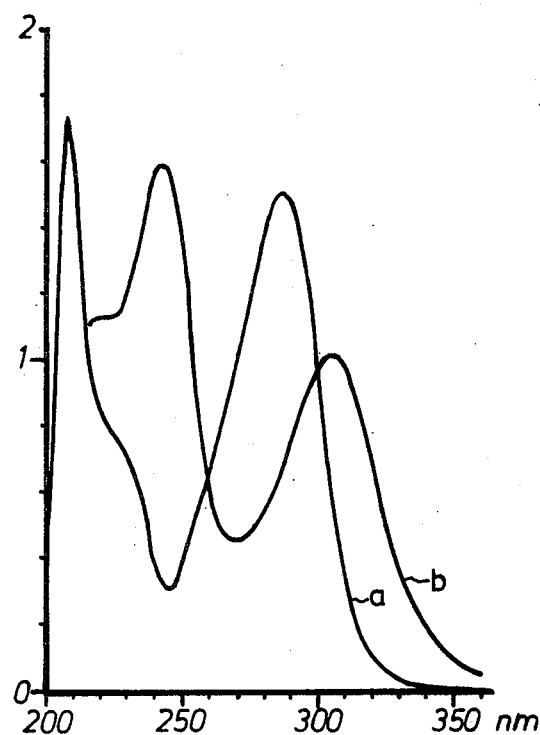
FIG. 1 is a plot of the UV spectrum of Nikkomycin recorded (a) in 1 N hydrochloric acid and (b) in 0.1 N sodium hydroxide solution. The ordinate gives the extinction and the abscissa gives the wavelength (nm units).
Figure 2:
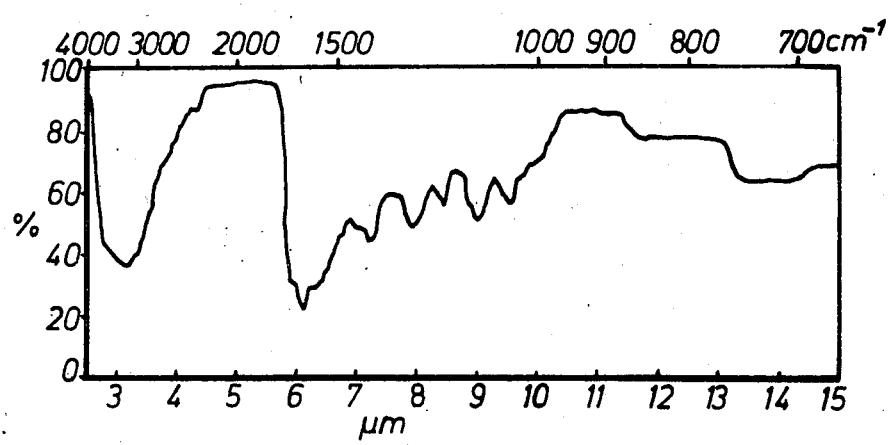
FIG. 2 shows the IR spectrum of Nikkomycin recorded in potassium bromide. The ordinate shows the transmission in % and the abscissa shows the wave number (cm$^{-1}$) and the wavelength ($\mu$m units).

(b) The UV spectrum and the IR spectrum are available (see the corresponding representations in FIGS. 1 and 2).

(c) With the aid of mass spectrometry and chemical degradation by acid hydrolysis it was possible to detect uracil, an amino-hexuronic acid and a new aminoacid containing a pyridine ring.

(d) Paper electrophoresis: the antibiotic is amphoteric. At a pH value of about 6, the distance migrated is small and the isoelectric point is thus probably located at this pH value. The table which follows, in which the distances migrated in paper electrophoresis are given as a function of the pH values of the buffer system, shows the behavior of the Nikkomycin mixture on electrophoresis.

| Buffer | pH | Time (minutes) | Distance migrated (mm) |
|---|---|---|---|
| Pyridine/glacial acetic acid | 3.9 | 60 | −12 |
| Pyridine/glacial acetic acid | 6.1 | 60 | −1 |
| Barbital* | 8.9 | 60 | +16 |

(*Barbital is 5,5-diethyl-barbituric acid)

(e) Thin layer chromatography: Three ninhydrin-positive spots, of which, in each case, only one spot corresponds to the substances which is active in the bioautogram, are found in all the solvent systems used which contain acetic acid. This fact could be ascribed to the lability of the antibiotic in acetic acid solution. In neutral solvent systems, only one ninhydrin-positive spot is found in each case.

(f) The following structural formula is proposed for Nikkomycin:

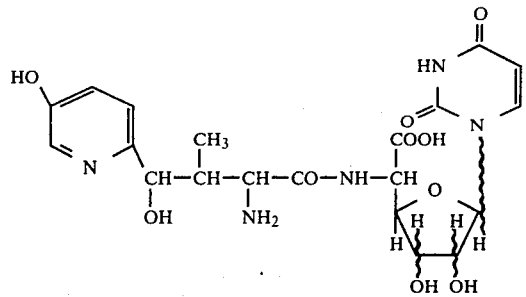

Elementary analysis of Nikkomycin gave the following values: C 48.21; H 5.08; N 13.58; O 31.58. An elementary composition of $C_4H_5NO_2$ is calculated from these figures. Cryoscopic determination gave a molecular weight of 404. However, the structure proposed here for Nikkomycin corresponds to a molecular weight of 495 and the formula $C_{20}H_{25}N_5O_{10}=(C_4H_5NO_2)_5$. The elementary composition calculated therefrom gives C 48.49%; H 5.09%; N 14.14%; O 32.29%.

(g) In contrast to the polyoxines which are known from the literature (see J. Am. Chem. Soc. 91, 7490 [1971]) and which are closest to Nikkomycin, there is no azacyclobutane radical in Nikkomycin. Neither of the polyoxines described contains the heterocyclic aminoacid.

It is considered that the Nikkomycin mixture can be sufficiently characterized by the features mentioned in paragraphs (a), (c) and (d), together with the IR and UV spectra and its constituent elements.

The characteristics correspond to the data in U.S. Pat. No. 4,046,881. As has been found in the intervening period, they also apply to a mixture of structurally different Nikkomycins which have not been described hitherto. Accordingly, the invention also relates to antibiotic Nikkomycins of the general formula

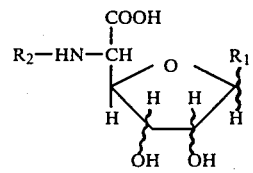

in which $R_1$ denotes

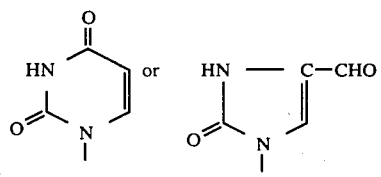

and $R_2$ denotes hydrogen,

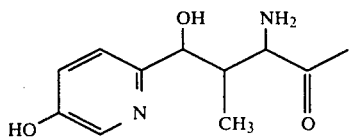

-continued or

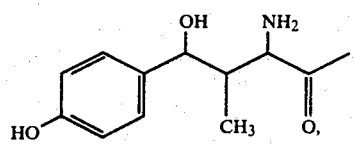

with the proviso that if $R_1$ denotes

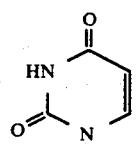

then $R_2$ cannot be

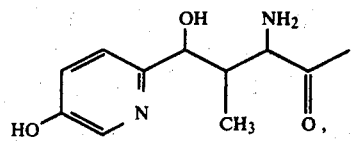

and their use as agents for combating pests.

The invention preferentially relates to the following active compound components or pairs of active compound components and to their use as agents for combating pests:

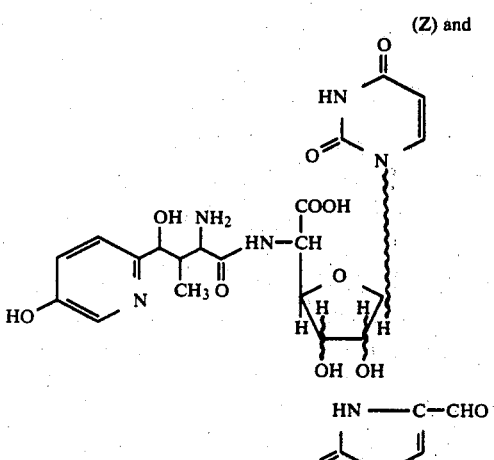   (Z) and   (a)

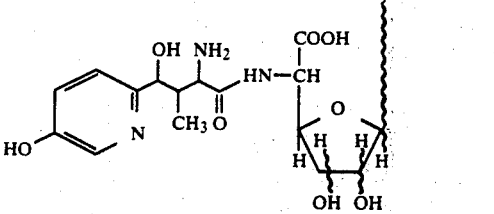   (X)

-continued

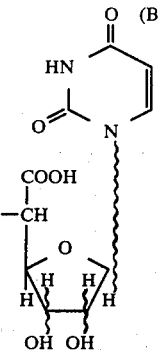   (B) and   (b)

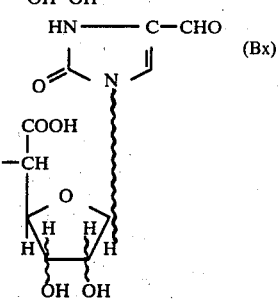   (Bx)

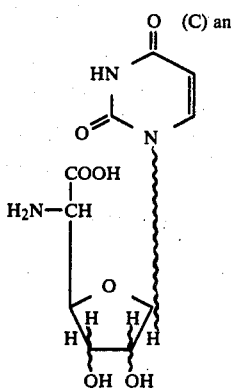   (C) and   (c)

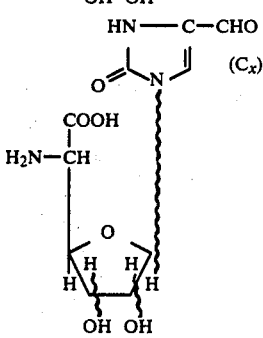   (Cx).

The Nikkomycin mixture and its components or pairs of components surprisingly display an excellent action against animal pests, especially against insects and arachnids.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederea,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

In the case of insects, the active compounds according to the invention have the effect of rendering treated plants unappetising and have a development-retarding and development-inhibiting action. In the case of spider mites, the use of Nikkomycin mixtures or Nikkomycin components effects slow extermination of a population after only a few treatments. In particular, depending on the time of application, a virtually stages inhibition of further development in the dormant periods nymphochrysalis, deutochrysalis and teleiochrysalis takes place; this is an effect which has not been known hitherto with other natural substances or microbial metabolites. The addition of other active compounds with a synergistic or additive effect is not necessary. Nikkomycin is also outstandingly effective against spider mites which are resistant to phosphoric acid esters. The low oral toxicity to mammals (LD 50 > 2000 mg/kg for rats) is a further advantage.

The preparation of the Nikkomycin mixtures is illustrated by the following examples wherein reagents, auxiliaries and technical equipment from the following firms are mentioned, in some cases by the tradename:

(a) Fermenters from New Brunswick Scientific Corporation Inc., New Brunswick, N.J., U.S.A.

(b) Hyphlo Supercel, Johns Mansville, Calif., U.S.A.

(c) Filter presses C 150 and U 1000 from Schenck, Filterbau, Schwäbisch-Gmünd, Federal Republic of Germany.

(d) Dowex, trademark of Dow Chemical Co., Midland, Mich., U.S.A.

(e) Amberlite, trademark Rohm and Haas Co., Philadelphia, Pa., U.S.A.

(f) SP-Sephadex, trademark Pharmacia Fine Chemicals, Upsala, Sweden.

(g) Uvicord II, LKB, Bromma, Sweden.

EXAMPLE 1

The nutrient solution in which the production strain *Streptomyces tendae* TÜ 901 was cultivated contained 2% of soya flour and 2% of mannitol; before sterilizing, the pH was adjusted to a pH of 7.5. $10 \times 500$ ml conical flasks which had 1 puncture point in the side and which each contain 100 ml of nutrient solution were inoculated with the production strain and incubated for 48 hours at 27° C. on a rotary shaking machine at 120 revolutions/minute. A 10 liter fermenter ("New Brunswick"), which contained 10 liters of nutrient solution, was inoculated with this pre-culture and incubated for 48 hours at 27° C., at 220 revolutions/minute and with an air supply of 4 liters/minute. A 100 liter fermenter ("New Brunswick"), which contained 100 liters of nutrient solution, was inoculated with the contents of this pre-fermenter and incubated for 78 hours at 27° C., at 150 revolutions/minute and with an air supply of 450 liters/minute.

With the addition of 2% of a filter aid (Hyphlo Supercel, from Johns Mansville), the culture was pressed out with a filter press, first through a pre-clarification filter (C 150, Schenk) and then through a post-clarification filter (U 1000, Schenk). The clear culture filtrate was acidified to pH 4.0 with acetic acid and introduced into a column ($100 \times 450$ mm) packed with Dowex 50 W $\times$ 4 (50-100 mesh, Na+ form). The flow rate was 10 liters/hour. The column was washed with deionized water until the liquid which issued from the column was completely colorless. The antibiotic was eluted with 30 liters of 0.01 N ammonia and 30 liters of 0.05 N ammonia. The biologically active eluate was freed from ammonia in a rotary evaporator, acidified to pH 4.0 with acetic acid and introduced into a column ($70 \times 900$ mm) packed with "Amberlite 252" (Na+ form). The flow rate was 5 liters/hour. The column was washed with deionized water until the liquid which issued from the column was completely colorless. The antibiotic was eluted with 15 liters of 0.05 N ammonia. The biologically active eluate was freed from ammonia in a rotary evaporator, concentrated to a small volume (1 liter), acidified to pH 4.0 with acetic acid and introduced into a column ($25 \times 850$ mm) packed with SP-Sephadex C-25. The flow rate was 100 ml/hour. The column was washed with deionized water until no further absorption was indicated in the UV flow detector at 280 nm (Uvicord II, LKB). Impurities were eluted with 0.01 M pyridine/acetate buffer (pH 4.7) and the antibiotic was eluted with 0.02 M pyridine/acetate buffer (pH 4.7). The biologically active fractions were combined, freed from buffer in a rotary evaporator and concentrated to a very small volume. The concentrate (10 ml) was introduced into a column ($25 \times 1500$ mm) packed with Bio-Gel P 2 (200–400 mesh) and eluted with deionized water. The flow rate was 100 ml/hour. In order to check the purity, detection with a UV flow detector was carried out at 280 nm. The biologically active fractions were combined and lyophilized in a freeze-drying installation.

The isolation of the components according to the invention from the Nikkomycin mixture prepared in this way is illustrated below using Nikkomycins X and Z as an example.

EXAMPLE 2

Isolation of Nikkomycin Z 10 ml of a saturated, aqueous dimedone solution were added to 100 mg of Nikkomycin and the mixture was warmed at 50°–70° C. on a water bath for 10 minutes and then left to stand for 20 hours at room temperature.

After evaporating in a rotary evaporator, the residue was taken up in 1 ml of $H_2O$ and subjected to chromatography on a column (0.9×60 cm) containing cellulose (Avicel, Messrs. Merck) using solvent system A. The orange-red dimedone derivative of X was eluted together with excess dimedone before Z. The fractions containing Z were combined and re-chromatographed on the same column. Yield: 11.4 mg of Z.

EXAMPLE 3

Isolation of Nikkomycin X 19 g of Nikkomycin were dissolved in 75 ml $H_2O$ and 9 g of alkylamines/CPG-1350 (Pierce Chem. Comp.) were added. After degassing in vacuo, the mixture was left to stand for 24 hours at room temperature. The carrier material was filtered off, washed out with 800 ml of $H_2O$ and treated with 100 ml of 5% acetic acid for 30 minutes at room temperature. The filtrate was lyophilized. 116 mg of residue were obtained and this was then subjected to chromatography on LiChroprep RP-8 using methanol/$H_2O$ (30:70). Yield of X (after lyophilisation): 18 mg.

EXAMPLE 4

Determination of the ratio of Nikkomycin X to Nikkomycin Z (a) By means of $^1$H-NMR spectroscopy In the $^1$H-NMR spectrum, Nikkomycin Z could be discerned by the two protons, which couple with one another, in position 5 ($\delta = 5.91$; d; 8 Hz) and position 6 ($\delta = 7.59$; d; 8 Hz). These two resonances are lacking in Nikkomycin X. Instead of these, two singlets occur at $\delta = 7.69$ and $\delta = 9.33$. By comparing the integrals of these signals, it was possible to determine the ratio of Nikkomycin X to Nikkomycin Z in the mixture.

(b) By means of high-pressure liquid chromatography

The two Nikkomycins X and Z could be separated on a RP-18 column (Merck, 10 and 250×4.6 mm) using a 0.005 molar solution of 1-hexanesulphonic acid in methanol/$H_2O$/acetic acid (14/84/2) as the eluent and determined quantitatively by means of UV detection at 280 nm. This determination could be carried out direct from the culture filtrate.

The insecticidal and acaricidal activity of the Nikkomycin mixture and its components is illustrated by the following biological examples:

EXAMPLE 5

Long-term test with *Pieris brassicae* (cabbage worm)

Treated cabbage plants were placed in a cage and infested with caterpillars in the 2nd stage. The test was discontinued when all of the caterpillars in the untreated control had pupated (after 15 days). Delay in development and destructive effect:

| % of preparation | % mortality after 15 days |
|---|---|
| 0.025: 0 pupae, 0 prepupae 6 larvae | 63 |
| 0.01: 0 pupae, 3 prepupae 5 larvae | 50 |
| Control: 13 pupae, 2 prepupae 1 larva | 0 |

EXAMPLE 6

Long-term test with *Laphygma exigua* (army worm)

The test used was as in Example 5.

There was no destructive effect; on the other hand, as a result of the action of the preparation, the development period from the $L_2$ larva to the winged insect was extended by 1–3 days, the weight of the pupae was reduced by 5–10% and the egg production was reduced by about 50%.

EXAMPLE 7

Long-term test with *Myzus persicae* (green peach aphid)

Using identical starting populations, the degree of $$\text{reproduction} = \frac{\text{number of animals after 9 days}}{\text{number of animals after 4 days}}$$

was tested. With 0.1% of the preparation, it was 1.9 and, accordingly, was slightly lowered compared with the control, for which it was 2.4.

EXAMPLE 8

Long-term test with *Megoura viciae* (vetch aphid)

The tests with *Megoura viciae* were carried out on potted field bean plants (*Vicia faba*, variety "Saxa") under laboratory conditions. The test animals were transferred to the test plants only after the plants had been treated and the spray coating had dried on. The tests were as a rule evaluated 5 days after the start of the test, calculated from the time at which the test animals were introduced.

As the results in the following Table 1 show, the mortality of adult animals was not very greatly influenced by Nikkomycin, while the reproduction, measured by the number of larvae produced per female and per day was reduced by 40% by 1000 and 500 ppm. The high mortality of the larvae produced was particularly noticeable. 1000 ppm completely prevented the development of a new population. Almost 60% of the larvae produced were not viable animals and these have been designated "amorphous" larvae in the tables. Some of the animals exhibited such extensive morphogenetic damage that they could hardly still be regarded as larvae. Very good results were still achieved even with 500 and 100 ppm.

The mortality of the larvae which had developed normally was more than 90% during the ecdysis stages, especially of larval stages 2 and 3. Because of the morphogenetic disorders (incompletely developed limbs or limbs struck or grown together) the larvae were not able to hatch from the exuvia.

TABLE 1

Effect of Nikkomycin on the mortality and reproduction of *Megoura viciae* and on the viability of the larvae during a 5-day test

| Concentration in ppm | Mortality of adult animals (%) | Total reproduction rate (%) | Reproduction rate larvae/adult/day | Mortality of the larvae (%) | Amorphous larvae % |
|---|---|---|---|---|---|
| 1000 | 12.50 | 53.60 | 3.0 | 100 | 59.57 |
| 500 | 9.37 | 68.91 | 3.9 | 99.27 | 55.43 |
| 100 | 19.66 | 84.60 | 4.8 | 92.65 | 42.26 |
| 10 | 19.23 | 82.70 | 4.7 | 5.23 | 0 |
| Control | 16.22 | 100 | 5.7 | 0.99 | 0 |

EXAMPLE 9

Stage tests with *Tetranychus urticae* (common two-spotted spider mites)

Bean plants were infested with, in each case, different stages of spider mites of the species *Tetranychus urticae* (resistant to phosphoric acid esters) and the development of the stages was monitored every 2–3 days. The following stages were used for the test and treated on bean plants: adults ♂ ♂ and ♀ ♀, eggs and mobile larval stages.

With dosages of between 0.02 and 0.004% of the non-formulated active compound, the development was in each case stopped at the following dormant stage (nymphochrysalis, deutochrysalis or teleiochrysalis).

EXAMPLE 10

Comparison of the action on *Tetranychus urticae* of normal sensitivity with the action on resistant *Tetranychus urticae*

Bean plants infested with eggs of a *Tetranychus urticae* strain of normal sensitivity and with eggs of a *Tetranychus urticae* strain which was resistant to phosphoric acid esters were treated with different dosages of Nikkomycin and the further development was observed every 2–3 days until the adult stage was reached in the untreated control. With an active compound concentration of 0.02–0.004%, development of the spider mites of normal sensitivity and of the resistant spider mites proceeded in the same way until the nymphochrysalis stage was reached; no protonymphs then hatched from this stage.

EXAMPLE 11

Field test against *Panonychus ulmi* (fruit tree spider mite)

In order to confirm the actions found in the laboratory for Nikkomycin in the field and on a different species of spider mite, in each case two apple trees were treated with different concentrations of Nikkomycin with the addition of a wetting agent. *Panonychus ulmi* in all stages were present on the leaves at the time of treatment. The number of surviving mobile stages was reduced by 94%, compared with the untreated control, by three spray treatments with 0.005% of Nikkomycin active compound.

It will be appreciated that the instant specification and examples are set forth by way of illustration and not limitation, and that various modifications and changes may be made without departing from the spirit and scope of the present invention.

What is claimed is:

1. A method of combating arthropods, comprising applying to the arthropods an arthropodicidally effective amount of an antibiotic which (a) is colorless, very readily soluble in water and in pyridine but insoluble in other customary organic solvents, gives a positive reaction with ninhydrin, sodium metaperiodate/benzidine and potassium permanganate and gives a yellow coloration with iron (III) chloride, (b) has the UV and IR spectra substantially as shown in FIGS. 1 and 2, (c) on chemical degradation yields uracil, an amino-hexuronic acid and an amino-acid containing a pyridine ring, (d) on paper electrophoresis proves to be an amphoteric substance and has an isoelectric point at about pH 6 and (e) consists of the elements carbon, hydrogen, oxygen and nitrogen, or one or more active components of the antibiotic mixture, the active agent being applied alone or in admixture with a diluent or carrier.

2. A method according to claim 1, wherein the active agent comprises at least one component of the formula

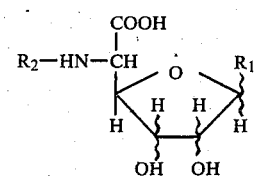

in which $R_1$ is

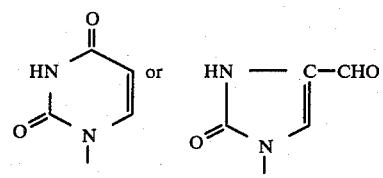

and $R_2$ is hydrogen,

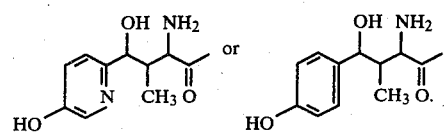

3. A method according to claim 1, wherein the active agent comprises at least one of the following pairs of components:

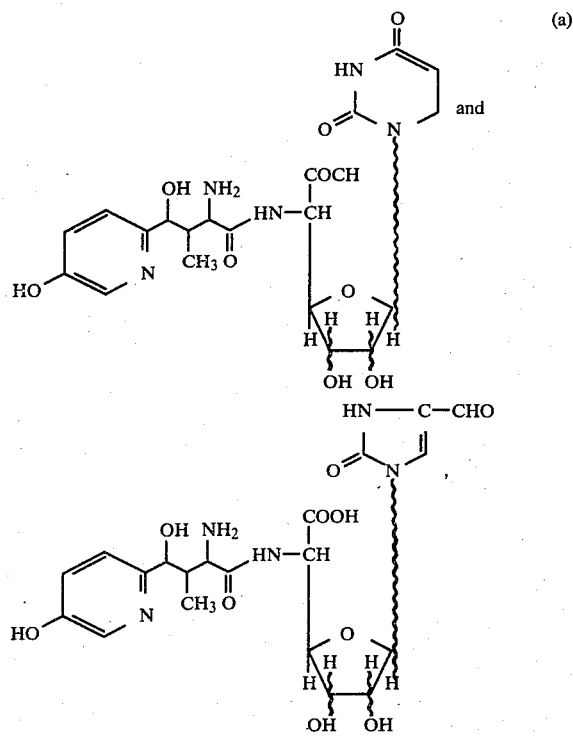

-continued
(b) 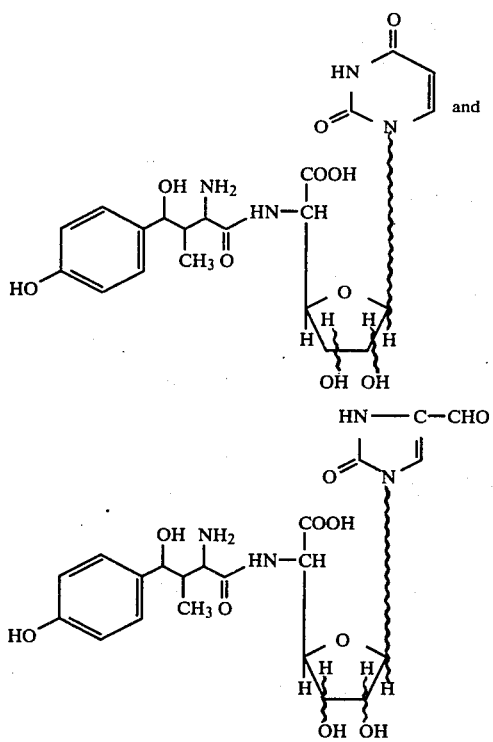
or
(c) 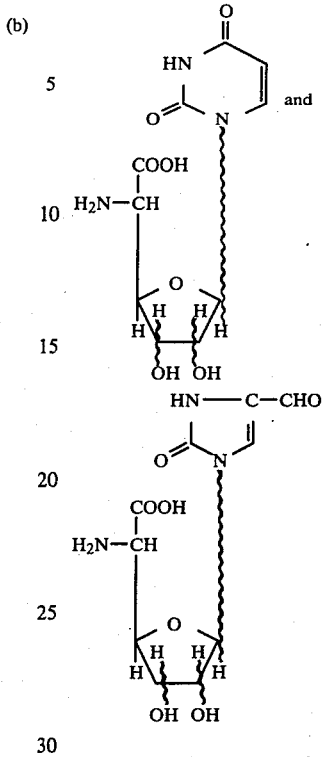
4. A method according to claim 1, wherein the arthropods are insects or acarids.
* * * * *